(12) United States Patent
Chen et al.

(10) Patent No.: US 11,475,798 B2
(45) Date of Patent: Oct. 18, 2022

(54) SIMULATION DEVICE FOR CHARACTERIZING AERODYNAMICS OF DRY POWER INHALANTS IN RESPIRATORY SYSTEM

(71) Applicant: Zhuhai Resproly Pharmaceutical Technology Co., Ltd, Zhuhai (CN)

(72) Inventors: Yongqi Chen, Zhuhai (CN); Fang Hu, Zhuhai (CN)

(73) Assignee: ZHUHAI RESPROLY PHARMACEUTICAL TECHNOLOGY CO., LTD., Zhuhai (CN)

( * ) Notice: Subject to any disclaimer, the term of this patent is extended or adjusted under 35 U.S.C. 154(b) by 357 days.

(21) Appl. No.: 16/898,256

(22) Filed: Jun. 10, 2020

(65) Prior Publication Data
US 2020/0394937 A1 Dec. 17, 2020

(30) Foreign Application Priority Data
Jun. 11, 2019 (CN) .......................... 201910502290.2

(51) Int. Cl.
*G09B 23/30* (2006.01)
*G01N 15/02* (2006.01)
(Continued)

(52) U.S. Cl.
CPC .............. *G09B 23/30* (2013.01); *G01N 15/02* (2013.01); *G01N 15/04* (2013.01); *G01N 30/02* (2013.01); *G01N 2030/027* (2013.01)

(58) Field of Classification Search
CPC .... G01N 15/0272; G01N 15/02; G01N 15/04; G01N 30/02; G01N 2015/0288; G01N 2015/0046; G01N 2030/027; A61P 11/00; G09B 23/288; G09B 23/30; A61M 15/009; A61M 15/0005; A61M 15/0036;
(Continued)

(56) References Cited

U.S. PATENT DOCUMENTS

| 5,584,701 A * | 12/1996 | Lampotang | .......... G09B 23/285 434/262 |
| 6,575,160 B1 * | 6/2003 | Volgyesi | ........... A61M 15/0045 128/203.15 |

(Continued)

*Primary Examiner* — Sang H Nguyen
(74) *Attorney, Agent, or Firm* — Tutunjian & Bitetto, P.C.

(57) ABSTRACT

The present invention discloses a simulation device for characterizing aerodynamics of dry powder inhalation in respiratory system comprising: a constant temperature-and-humidity chamber, a steam and vacuum generating device and a respiratory system model arranged in the constant temperature and humidity chamber, and the constant temperature and humidity chamber and the respiratory system model are both connected with the steam and vacuum generating device; a temperature and humidity sensor is arranged in the constant temperature-and-humidity chamber and electrically connected with the steam and vacuum generating device; the respiratory system model comprises an oral cavity receiver and sample collectors, wherein inner walls of the respiratory system model are coated with a coating, the sample collectors includes a first sample collector and a second sample collector, each of the collectors is provided with 8 collecting trays.

7 Claims, 1 Drawing Sheet

(51) Int. Cl.
*G01N 15/04* (2006.01)
*G01N 30/02* (2006.01)

(58) Field of Classification Search
CPC ............ A61M 15/0033; A61M 11/042; A61M 16/04; A61M 16/1075; A61M 2205/8206; A61M 2205/36; A61M 2205/3368
See application file for complete search history.

(56) References Cited

U.S. PATENT DOCUMENTS

| | | | |
|---|---|---|---|
| 9,737,518 B2 * | 8/2017 | Sung | A61P 11/00 |
| 2009/0084379 A1 * | 4/2009 | Goeckner | A61M 15/0043 128/203.15 |
| 2013/0266653 A1 * | 10/2013 | Lipp | A61K 39/395 424/489 |
| 2016/0217709 A1 * | 7/2016 | Minskoff | G09B 23/30 |
| 2016/0228658 A1 * | 8/2016 | Minskoff | A61M 15/009 |

* cited by examiner

SIMULATION DEVICE FOR CHARACTERIZING AERODYNAMICS OF DRY POWER INHALANTS IN RESPIRATORY SYSTEM

CROSS REFERENCE TO RELATED APPLICATION

This application claims the priority of Chinese Patent Application No. 201910502290.2 entitled "Simulation Device for Characterizing Aerodynamics of Dry Powder Inhalation in Respiratory System" filed with the Chinese Patent Office on Jun. 11, 2019, which is incorporated herein by reference in its entirety.

TECHNICAL FIELD

The present invention relates to the field of medical research equipment, in particular to a simulation device for aerodynamics of a respiratory system, and especially relates to a simulation device for characterizing aerodynamics of dry powder inhalation in respiratory system.

BACKGROUND ART

Dry powder inhalations (DPI) are preparations which are prepared by powdering medicaments or a medicament auxiliary materials and then actively inhaled through a mouth of a patient by virtue of a specific administration device, and the medicament powder is inhaled into a respiratory system by an air flow generated from the patient actively inhaling, so as to have therapeutic effect. The preparations are composed of a powder preparation and a corresponding administration device, and the therapeutic effect of the preparations is influenced by various factors such as a powder prescription, an inhalation device, inhalation skill of a patient, aerodynamic particle sizes of the medicaments and the like.

Among them, the aerodynamic particle size is one of the most important properties reflecting lung deposition and ultimate therapeutic effect. It is generally believed that when the aerodynamic particle sizes of the medicament are in a range of 1-5 μm, the particles can reach a peripheral airway of the most effective absorption site; the particles larger than 10 μm generally deposit in the mouth or throat, and the particles smaller than 0.5 μm do not deposit and continue to move forward with Brownian motion.

As is well known, medicament research & development and industrialization require a large amount of capital and a long period, and particularly, new medicaments require at least 1 billion yuan and 10 years before they can be marketed, and even if generic medicaments which are generally believed to be relatively simple also require at least 50 million yuan and 5 years before they can be marketed. The inhalation preparation is a medicament dosage form with the largest difficulty, the highest technical threshold and larger investment in all the medicament dosage forms. Due to the complexity of a respiratory tract structure and the complexity of particle aerodynamics, a reasonable administration result can only be obtained based on sufficiently knowing and understanding inhalation technology characteristics, engineering mechanics, the characteristics of the inhalation device, aerodynamic characteristics, inhalation safety of auxiliary materials, in vivo-in vitro correlation and the like.

However, in the prior art, aerodynamic behavior of the medicament is generally characterized by using devices such as Andersen Cascade Impactor (ACI) and Next Generation Impactor (NGI). Since in such devices, a connection between an airway and the throat is characterized as a right angle, and the airway and the throat are made of smooth stainless steel pipes, the powder of medicament and auxiliary materials when passing through the throat, the airway and other parts under the action of vacuum pump, is slightly adhered. It is eventually showed that most of the medicament is passed through the throat, airway and other parts to enter the lung, and thus the lung deposition conditions of different grades can be obtained. Such device for characterizing the aerodynamic behavior of the material has a great difference from the real human body condition, so that when the new medicaments or the generic medicaments are made, even if the aerodynamic characterization of the generic medicines and the original research medicines are consistent, since an in-vitro test in such devices can not directly correspond to an in-vivo therapeutic effect, a situation occurs that a difference of in-vivo therapeutic effect between the generic medicines and the original research medicines is very great, and thus a clinical risk is increased.

Therefore, it is necessary to design a simulation device close to a respiratory system of human body so as to meet a requirement of researching medicaments.

SUMMARY

The technical problem to be solved by the present invention is to provide a simulation device for characterizing aerodynamics of dry powder inhalation in respiratory system, the device is close to the human respiratory system.

In order to solve the above technical problems, the technical solutions of the present invention are as follows.

A simulation device for characterizing aerodynamics of dry powder inhalation in respiratory system, comprising: a constant temperature-and-humidity chamber, a steam and vacuum generating device and a respiratory system model, wherein the respiratory system model is arranged in the constant temperature-and-humidity chamber, and the constant temperature-and-humidity chamber and the respiratory system model are both connected with the steam and vacuum generating device; a temperature and humidity sensor is arranged in the constant temperature and humidity chamber and electrically connected with the steam and vacuum generating device; the respiratory system model comprises an oral cavity receiver and a sample collectors, wherein inner walls of the respiratory system model are coated with coatings which become sticky after absorbing moisture, the sample collectors include a first sample collector and a second sample collector, each of the collectors is provided with 8 collecting trays, and the first sample collector and the second sample collector are connected with the oral cavity receiver through a conduit imitating the shape of a human respiratory tract.

Preferably, the steam and vacuum generating device comprises a vacuum pump, a steamer and a temperature and humidity control valve, the vacuum pump is connected with the first sample collector and the second sample collector through a pipeline which is provided with a flow regulating valve, and the vacuum pump is connected with a pressure regulating valve, a vacuum regulating valve and a timer which are arranged in the steam and vacuum generating device.

Preferably, the steamer is provided with the temperature and humidity control valve.

Preferably, the steamer is connected with the constant temperature-and-humidity chamber through a duct to adjust a temperature and a humidity of the constant temperature- and humidity-chamber.

Preferably, a display screen for displaying the temperature, the humidity and a saturation time are provided on an outside surface of the constant temperature-and-humidity chamber, and a humidity bleeder valve is provided at a bottom of the constant temperature-and-humidity chamber. When the humidity of the constant temperature-and-humidity chamber is too high, the humidity bleeder valve is opened to adjust.

Preferably, respectively at a bottom of the first sample collector and at a bottom of the second sample collector, filters are provided, which are dehumidifying filters that can remove moisture in the hot humid air before it enters the vacuum pump, so that the vacuum pump is protected.

Preferably, the sample collectors are internally provided with level 0-level 7 collecting trays, and a diameter of each filter hole of level 0 collecting tray is larger than 9 μm, a diameter of each filter hole of level 1 collecting tray is 5.8-9 μm, a diameter of each filter hole of level 2 collecting tray is 4.7-5.8 μm, a diameter of each filter hole of level 3 collecting tray is 3.3-4.7 μm, a diameter of each filter hole of level 4 collecting tray is 2.1-3.3 μm, a diameter of each filter hole of level 5 collecting tray is 1.1-2.1 μm, aperture diameter of each filter hole of level 6 collecting tray is 0.7-1.1 μm, a diameter of each filter hole of level 7 collecting tray is 0.4-0.7 μm, and exhaust channels are provided around each of the collecting trays.

The micro powder with particle sizes of more than 9 μm can be collected by the level 0 collecting tray, the micro powder with particle sizes of 5.8-9 μm can be collected by the level 1 collecting tray, the micro powder with particle sizes of 4.7-5.8 μm can be collected by the level 2 collecting tray, the micro powder with particle sizes of 3.3-4.7 μm can be collected by the level 3 collecting tray, the micro powder with particle sizes of 2.1-3.3 μm can be collected by the level 4 collecting tray, the micro powder with particle sizes of 1.1-2.1 μm can be collected by the level 5 collecting tray, the micro powder with particle sizes of 0.7-1.1 μm can be collected by the level 6 collecting tray, and the micro powder with particle sizes of 0.4-0.7 μm can be collected by the level 7 collecting tray. And the micro powder with larger particle sizes are trapped in a low-level collecting tray, and the micro powder with smaller particle sizes continuously move to the next collecting tray, so that the micro powder with different particle sizes are distributed in level 0-level 7 collecting trays respectively.

By adopting the above technical solutions, the simulation device comprises the steam and vacuum generation device which is connected with the constant temperature-and-humidity chamber and the respiratory system model, and the construction of the respiratory system model is close to that of the human respiratory system, the inner walls of the respiratory system model use the coatings which become sticky after absorbing moisture, and the simulation device can generate the same temperature and humidity environment as that in a human body, so that the simulation device when characterizing dry powder inhalation is closer to the real human respiratory system. In addition, the use of filters with different levels enables the simulation device to be used for researching the deposition conditions of dry powder inhalation with different particle sizes, reducing a risk of inaccurate data caused by large difference between simulation environment and human body environment and the clinical risk caused by using the inaccurate data. Therefore, the present invention can more accurately and scientifically compare the aerodynamic characteristics of the generic medicines and the original medicines, improve the accuracy and the correlation of in-vivo data derived from in-vitro data and, reduce clinical risks and reduce huge capital investment.

Figure 1:
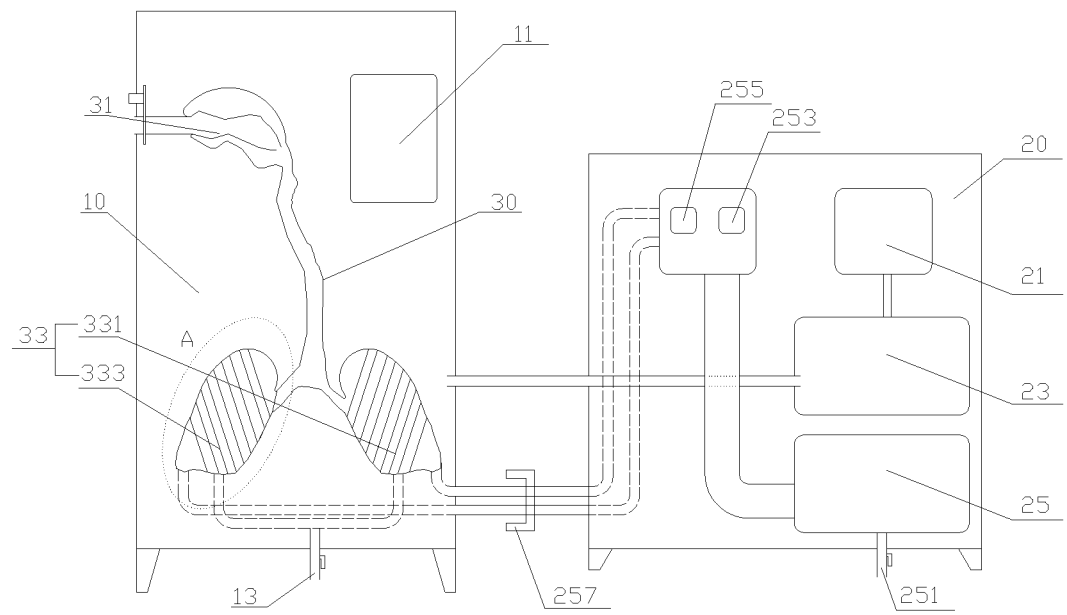
FIG. 1 is a schematic view of the structure of the present invention.

Reference numerals: 10—constant temperature-and-humidity chamber, 11—display screen, 13—humidity bleeder valve, 20—steam and vacuum generating device, 21—temperature and humidity control valve, 23—steamer, 25—vacuum pump, 30—respiratory system model, 31—oral cavity receiver, 33—sample collector, 33a—level 0 collecting tray, 33b—level 1 collecting tray, 33c—level 2 collecting tray, 33d—level 3 collecting tray, 33e—level 4 collecting tray, 33f—level 5 collecting tray, 33g—level 6 collecting tray, 33h—level 7 collecting tray, 33J—filter, 33u—exhaust passage, 251—pressure regulating valve, 253—vacuum regulating valve, 255—timer, 257—flow control valve, 331—first sample collector, 333—second sample collector.

DETAILED DESCRIPTION OF THE EMBODIMENTS

Now, further description of specific embodiments of the present invention will be made with reference to the accompanying drawings. It should be noted that the description of the embodiments is provided to help understanding of the present invention, and does not intended to limit the present invention. In addition, technical features involved in various embodiments of the present invention described below may be combined with each other as long as they do not conflict with each other.

Figure 2:
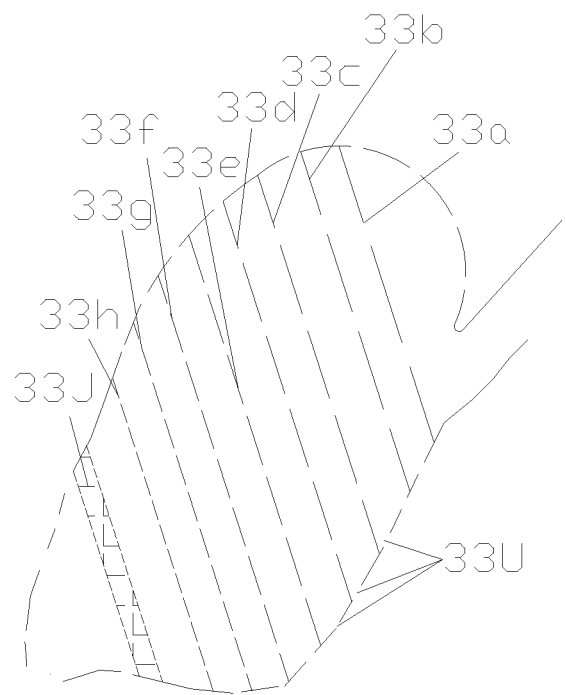
FIG. 2 is an enlarged view of a portion A in FIG. 1.

As shown in FIG. 1 and FIG. 2, a simulation device for characterizing aerodynamics of dry powder inhalation in respiratory system comprises a constant temperature-and-humidity chamber 10, a steam and vacuum generating device 20 and a respiratory system model 30, wherein the respiratory system model 30 is arranged in the constant temperature-and-humidity chamber 10, and the constant temperature-and-humidity chamber 10 and the respiratory system model 30 are both connected with the steam and vacuum generating device 20; a temperature and humidity sensor is provided in the constant temperature-and-humidity chamber 10 and electrically connected with the steam and vacuum generating device 20; the respiratory system model 30 comprises an oral cavity receiver 31 and sample collectors 33, inner walls of the respiratory system model 30 are coated with coatings which can become sticky after absorbing moisture, the sample collectors 33 includes a first sample collector 331 and a second sample collector 333, and one end of the first sample collector 331 and one end of the second sample collector 333 are connected with the oral cavity receiver 31 through a conduit imitating a shape of a human respiratory tract.

Further, the steam and vacuum generating device 20 includes a vacuum pump 25, a steamer 23, and a temperature and humidity control valve 21, the vacuum pump 25 is connected with the first sample collecting tray 331 and the second sample collecting tray 333 through a pipeline provided with a flow regulating valve 257, and the vacuum pump 25 is connected with a pressure regulating valve 251, a vacuum regulating valve 253, and a timer 255 which are arranged in the steam and vacuum generating device 20.

Wherein, the steamer 23 is provided with the temperature and humidity control valve 21.

Further, the steamer 23 is connected with the constant temperature-and-humidity chamber through a duct to adjust the temperature and humidity of the constant temperature-and-humidity chamber 10.

Wherein, a display screen 11 for displaying temperature, humidity and saturation time is provided on an outside surface of the constant temperature- and humidity-chamber, and a humidity bleeder valve 13 is provided at a bottom of the constant temperature-and-humidity chamber 10. When the humidity of the constant temperature-and-humidity chamber 10 is too high, the humidity bleeder valve 13 is started to adjust.

Further, respectively at a bottom of the first sample collector 331 and at a bottom of the second sample collector 333, filters 33J are both provided, which are dehumidifying filters 33J that can remove moisture from the hot humid air before it enters the vacuum pump, so that the vacuum pump is protected.

The sample collectors are internally provided with level 0-level 7 collecting trays, and a diameter of each filter pore in the level 0 collecting tray 33a is larger than 9 μm, a diameter of each filter pore in the level 1 collecting tray 33b is 5.8-9 μm, a diameter of each filter pore in a level 2 collecting tray 33c is 4.7-5.8 μm, a diameter of each filter pore in a level 3 collecting tray 33d is 3.3-4.7 μm, a diameter of each filter pore in a level 4 collecting tray 33e is 2.1-3.3 μm, a diameter of each filter pore in a level 5 collecting tray 33f is 1.1-2.1 μm, a diameter of each filter pore in a level 6 collecting tray 33g is 0.7-1.1 μm, a diameter of each filter pore in a level 7 collecting tray 33h is 0.4-0.7 μm, and exhaust channels 33u are provided around each of the collecting trays.

The micro powder with particle sizes of more than 9 μm can be collected by the level 0 collecting tray 33a, the micro powder with particle sizes of 5.8-9 μm can be collected by the level 1 collecting tray 33b, the micro powder with particle sizes of 4.7-5.8 μm can be collected by the level 2 collecting tray 33c, the micro powder with particle sizes of 3.3-4.7 μm can be collected by the level 3 collecting tray 33d, the micro powder with particle sizes of 2.1-3.3 μm can be collected by the level 4 collecting tray 33e, the micro powder with particle sizes of 1.1-2.1 μm can be collected by the level 5 collecting tray 33f, the micro powder with particle sizes of 0.7-1.1 μm can be collected by the level 6 collecting tray 33g, and the micro powder with particle sizes of 0.4-0.7 μm can be collected by the level 7 collecting tray 33h. And the micro powder with larger particle sizes are trapped in low level collecting trays, and the micro powder with smaller particle sizes continuously move to the next collecting tray, so that the micro powder with different particle sizes are distributed in level 0-level 7 collecting trays respectively.

The sample collectors simulate the lungs of a human body, and the collecting trays of different stages are used for collecting medicines of different particle sizes.

What is next to the filter connected to one end of the pipeline of the vacuum pump 25 is a 7th stage collecting tray, from which the levels of collecting trays gradually decreased to the level 0 collecting tray that is near one end of a pipeline connected with the oral receiver 31.

The following are functional descriptions of main components:
  oral cavity receiver 31: coupled to a DPI device with a medicine;
  display screen 11: displaying the constant temperature- and humidity control chamber and the saturation time after the required temperature and humidity being reached;
  respiratory system model 30: all inner walls thereof being coated with special coating which becomes sticky after absorbing moisture, the coating containing nano active substances such as nano titanium dioxide, the coating being able to absorb moisture and become sticky in an environment (internal environment in human body) of 75% RH and 37° C., and when passing through there, the micro powder being effectively absorbed without rebounding;
  steamer 23: providing warm steam for the constant temperature-and-humidity chamber;
  vacuum pump 25: negative pressure being able to generate in the respiratory system model, and the powder in the DPI device being actively sucked into the model;
  timer 255: recording a time for evacuating;
  flow control valve 257: regulating a suction volume of the vacuum pump;
  filter 33J: having a desiccator attached therein, the desiccator being able to adsorb moisture in the constant temperature-and-humidity chamber, so that a vacuum pump is prevented from sucking wet air; and
  first sample collector 331 and second sample collector 333: simulating a configuration of the lung.

The using method of the present invention comprises the following steps:
  step 1: starting the constant temperature-and-humidity chamber 10 and the steamer 23, and holding for 5-10 minutes for later use, after the temperature and the humidity reaching required temperature and the humidity;
  step 2: inserting the DPI device into the oral cavity receiver 31, setting a flow of the DPI device, turning on the vacuum pump 25 for evacuating, and setting an evaluation time according to characteristics of each powder product;
  step 3: closing the vacuum pump 25 after the set time elapsed, taking out the first sample collector 331 and the second sample collector 333, eluting the samples on each level of the sample collecting trays, and after the foregoing treatment, injecting into a liquid chromatograph for content determination, and obtaining the content of the medicines in each level of the sample collecting trays, and an aerodynamic particle size distribution profile.

Although the embodiments of the present invention have been described in detail with reference to the accompanying drawings above, the present invention is not limited to the described embodiments. It will be apparent to those skilled in the art that various changes, modifications, substitutions and alterations can be made in the embodiments without departing from the principles and spirit of the present invention, which are still within the scope of the present invention.

What is claimed is:

1. A simulation device for characterizing aerodynamics of dry powder inhalation in respiratory system, comprising: a constant temperature-and-humidity chamber, a steam and vacuum generating device and a respiratory system model, wherein the respiratory system model is arranged in the constant temperature-and-humidity chamber, and the constant temperature-and-humidity chamber and the respiratory system model are both connected with the steam and vacuum generating device; a temperature and humidity sensor is provided in the constant temperature-and-humidity chamber and electrically connected with the steam and vacuum generating device; the respiratory system model comprises an oral cavity receiver and sample collectors, inner walls of the respiratory system model are coated with coatings which become sticky after absorbing moisture, the sample collectors comprise a first sample collector and a second sample collector, each of the sample collectors is provided with 8 collecting trays, and the first sample collector and the second sample collector are connected with the oral cavity receiver through a conduit imitating a shape of a human respiratory tract.

2. The simulation device of claim 1, wherein the steam and vacuum generating device comprises a vacuum pump, a steamer and a temperature and humidity control valve, the vacuum pump is connected with the first sample collector and the second sample collector through a pipeline which is provided with a flow regulating valve, and the vacuum pump is connected with a pressure regulating valve, a vacuum regulating valve and a timer which are arranged in the steam and vacuum generating device.

3. The simulation device of claim 2, wherein the steamer is provided with the temperature and humidity control valve.

4. The simulation device of claim 3, wherein the steamer is connected with the constant temperature-and-humidity chamber through a duct.

5. The simulation device of claim 4, wherein a display screen for displaying temperature, humidity and saturation is provided on an outside of the constant temperature and humidity chamber, and a humidity bleeder valve is provided at a bottom of the constant temperature-and-humidity chamber.

6. The simulation device of claim 5, wherein filters are provided at a bottom of the first sample collector and at a bottom of the second sample collector respectively, and the filters are dehumidifying filters.

7. The simulation device of claim 6, wherein the sample collectors are internally provided with level 0-level 7 collecting trays, and a diameter of each filter hole of level 0 collecting tray is larger than 9 μm, a diameter of each filter hole of level 1 collecting tray is 5.8-9 μm, a diameter of each filter hole of level 2 collecting tray is 4.7-5.8 μm, a diameter of each filter hole of level 3 collecting tray is 3.3-4.7 μm, a diameter of each filter hole of level 4 collecting tray is 2.1-3.3 μm, a diameter of each filter hole of level 5 collecting tray is 1.1-2.1 μm, a diameter of each filter hole of level 6 collecting tray is 0.7-1.1 μm, a diameter of each filter hole of level 7 collecting tray is 0.4-0.7 μm, and exhaust channels are provided around each of the collecting trays.

* * * * *